United States Patent
Diroll et al.

(10) Patent No.: US 10,138,134 B1
(45) Date of Patent: Nov. 27, 2018

(54) METHOD FOR FABRICATION OF SUPERLATTICES AND APERIODIC LAYERED STRUCTURES USING SOLUTION DEPOSITION

(71) Applicant: UCHICAGO ARGONNE, LLC, Chicago, IL (US)

(72) Inventors: Benjamin Diroll, Chicago, IL (US); Richard D. Schaller, Clarendon Hills, IL (US)

(73) Assignee: UChicago Argonne, LLC, Chicago, IL (US)

(*) Notice: Subject to any disclaimer, the term of this patent is extended or adjusted under 35 U.S.C. 154(b) by 0 days.

(21) Appl. No.: 15/644,602

(22) Filed: Jul. 7, 2017

(51) Int. Cl.
| | |
|---|---|
| C01G 11/02 | (2006.01) |
| C23C 16/22 | (2006.01) |
| C23C 16/455 | (2006.01) |
| C09K 11/56 | (2006.01) |
| C09K 11/88 | (2006.01) |
| C07C 57/12 | (2006.01) |
| C01B 19/00 | (2006.01) |

(52) U.S. Cl.
CPC ............ C01G 11/02 (2013.01); C01B 19/007 (2013.01); C07C 57/12 (2013.01); C09K 11/565 (2013.01); C09K 11/883 (2013.01); C23C 16/22 (2013.01); C23C 16/45527 (2013.01); *C01P 2002/72* (2013.01); *C01P 2004/04* (2013.01)

(58) Field of Classification Search
CPC ... C01G 11/02; C23C 16/22; C23C 16/45527; C09K 11/883; C09K 11/565; C07C 57/12; C01B 19/007; C01P 2004/04; C01P 2002/72
See application file for complete search history.

(56) References Cited

PUBLICATIONS

Son et al., "Cation Exchange Reactions in Ionic Nanocrystals," Science 306 (5698), 1009-1012. (Year: 2004).*
Robinson et al., "Spontaneous Superlattice Formation in Nanorods Through Partial Cation Exchange," Science 317 (5836), 355-358. (Year: 2007).*
Luther et al., "Synthesis of PbS Nanorods and Other Ionic Nanocrystals of Complex Morphology by Sequential Cation Exchange Reactions," J. Am. Chem. Soc. 2009, 131, 16851-16857. (Year: 2009).*
Moon et al., "Chemical Transformation in Ultrathin Chalcogenide Nanowires," ACSNano, vol. 4, No. 4, 2307-2319. (Year: 2010).*
Arakawa & Sakaki, "Multidimensional quantum well laser and temperature dependence of its threshold current," Applied Physics Letters 40, pp. 939-941 (1982).
Battacharya & Dutta, "Quantum Well Optical Devices and Materials," Annual Review of Materials Science 23, pp. 79-123 (1993).

(Continued)

*Primary Examiner* — William P Fletcher, III
(74) *Attorney, Agent, or Firm* — Foley & Lardner LLP (57) ABSTRACT

A method for forming inorganic structures includes (a) transferring nanocrystals to a polar protic solvent using at least one chalcogenide precursor to produce a negatively-charged chalcogen-rich nanocrystal surface, (b) removing excess anions of the chalcogenide precursor, (c) introducing a metal salt to bind a divalent metal cation to the negatively-charged chalcogen-rich nanocrystal surface to regenerate a positively-charged metal-rich nanocrystal surface, and (d) removing excess divalent metal cations of the metal acetate salt.

9 Claims, 8 Drawing Sheets

(56) References Cited

PUBLICATIONS

Bauer & Van Der Merwe, "Structure and growth of crystalline superlattices: From monolayer to superlattice," Physical Review B 33, pp. 3657-3671 (1986).
Boldt, et al., "Synthesis of Highly Luminescent and Photo-Stable, Graded Shell CdSe/CdxZn1—xS Nanoparticles by In Situ Alloying," Chemistry of Materials 25(23), pp. 4731-4738 (2013).
Cossairt & Owen, "CdSe Clusters: At the Interface of Small Molecules and Quantum Dots," Chemistry of Materials 23(12), pp. 3114-3119 (2011).
Diroll, et al,. "Ultrafast Photoluminescence from the Core and the Shell in CdSe/CdS Dot-in-Rod Heterostructures," ChemPhysChem 17(5), pp. 759-765 (2016).
Fedin & Talapin, "Colloidal CdSe Quantum Rings," Journal of the American Chemical Society 138(31), pp. 9771-9774 (2016).
Garcia-Barriocanal, et al,. "Colossal Ionic Conductivity at Interfaces of Epitaxial ZrO2:Y2O3/SrTiO3 Heterostructures," Science 321, 5889, pp. 676-680 (2008).
Ithurria & Dubertret, "Quasi 2D Colloidal CdSe Platelets with Thicknesses Controlled at the Atomic Level," Journal of the American Chemical Society 130(49), pp. 16504-16505 (2008).
Ithurria & Talapin, "Colloidal Atomic Layer Deposition (c-ALD) using Self-Limiting Reactions at Nanocrystal Surface Coupled to Phase Transfer between Polar and Nonpolar Media," Journal of the American Chemical Society 134(45), pp. 18585-18590 (2012).
Ithurria, et al., "Colloidal nanoplatelets with two-dimensional electronic structure," Nature Materials 10, pp. 936-941 (2011).
Koehler, "Attempt to Design a Strong Solid," Physical Review B 2(2), pp. 547-551 (1970).
Lehoczky, "Retardation of Dislocation Generation and Motion in Thin-Layered Metal Laminates," Physical Review Letters 41(26), pp. 1814-1818 (1978).
Levine, "Quantum-well infrared photodetectors," Journal of Applied Physics 74(R1), (1993).
Li, et al., "Large-Scale Synthesis of Nearly Monodisperse CdSe/CdS Core/Shell Nanocrystals Using Air-Stable Reagents via Successive Ion Layer Adsorption and Reaction," Journal of the American Chemical Society 125(41), pp. 12567-12575 (2003).
Ma & Sasaki, "Organization of Artificial Superlattices Utilizing Nanosheets as a Building Block and Exploration of Their Advanced Functions," Annual Review of Materials Research 45, pp. 111-127 (2015).
Murray, et al., "Self-Organization of CdSe Nanocrystallites into Three-Dimensional Quantum Dot Superlattices," Science 270(5240), pp. 1335-1338 (1995).
Nag, et al., "Metal-free Inorganic Ligands for Colloidal Nanocrystals: S2—, HS—, Se2—, HSe—, Te2—, HTe—, TeS32—, OH—, and NH2— as Surface Ligands," Journal of the American Chemical Society 133(27), pp. 10612-10620 (2011).
Nakamura, et al,. "High-Brightness InGaN Blue, Green and Yellow Light-Emitting Diodes with Quantum Well Structures," Japanese Journal of Applied Physics 34(2), 7A (1995).
Pedetti, et al., "Optimized Synthesis of CdTe Nanoplatelets and Photoresponse of CdTe Nanoplatelets Films," Chemistry of Materials 25(12), pp. 2455-2462 (2013).
Razgoniaeva, et al., "Colloidal Synthesis of Monodisperse Semiconductor Nanocrystals through Saturated Ionic Layer Adsorption," Chemistry of Materials 26(8), pp. 2823-2833 (2016).
Robinson, et al., "Spontaneous Superlattice Formation in Nanorods Through Partial Cation Exchange," Science 317(5836), pp. 355-358 (2007).
Sagar, et al,. "PbS/CdS Core/Shell Quantum Dots by Additive, Layer-by-Layer Shell Growth," Chemistry of Materials 28(19), pp. 6953-6959 (2016).
She, et al., "Low-Threshold Stimulated Emission Using Colloidal Quantum Wells," Nano Letters 14(5), pp. 2772-2777 (2014).
Tessier, et al., "Efficient Exciton Concentrators Built from Colloidal Core/Crown CdSe/CdS Semiconductor Nanoplatelets," Nano Letters 14(1), pp. 207-213 (2014).
Vashaee & Shakouri, "Improved Thermoelectric Power Factor in Metal-Based Superlattices," Physical Review Letters 92, 106103, 4 pages (2004).

\* cited by examiner

METHOD FOR FABRICATION OF SUPERLATTICES AND APERIODIC LAYERED STRUCTURES USING SOLUTION DEPOSITION

STATEMENT OF GOVERNMENT INTEREST

The United States Government claims certain rights in this invention pursuant to Contract No. DE-AC02-06CH11357 between the U.S. Department of Energy and U. Chicago Argonne, LLC, as operator of Argonne National Laboratory.

FIELD OF THE INVENTION

The present invention generally relates to methods of fabrication of superlattices and aperiodic layered structures using solution deposition. Specifically, the present invention relates to sequential solution-phase deposition of single atomic layers of cations and anions using self-limiting chemical reactions to form periodic (e.g. superlattices) and aperiodic structures.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Superlattices are ordered arrangements of multiple distinct materials in which new or improved mechanical or electrical properties are achieved through controlled variation in the composition, scale, or superstructure (e.g. periodicity). These structures may be employed in a wide range of technologies including lasers, light emitting diodes (LEDs), photodetectors, fuel cells, and thermoelectric devices. Typically, the variation in composition of these materials is in only one dimension and the scale of composition variations is on the order of nanometers.

Conventionally, the majority of layered superlattice structures have been fabricated using techniques requiring gas-phase reagents, and often in high temperature, low pressure (high vacuum) environments (e.g., chemical or physical vapor deposition). These vapor-based methods have significant drawbacks including: cost and energy intensity, requirement of specially-designed substrates and expensive precursors of limited chemistries, difficulty or inability to deviate from planar processing, and limited chemical compositions.

Other solution-based techniques such as spin-coating or chemical bath deposition often sacrifice precision of thickness of the deposited layers. Further, bonding between successive layers is typically non-covalent in solution-based depositions, meaning that interfaces between materials may be very poor conductors of electricity.

A need exists for improved technology, including a method of fabrication of superlattices and aperiodic layered structures using solution deposition.

SUMMARY

In one embodiment, a method for forming inorganic structures includes (a) transferring nanocrystals to a polar protic solvent using at least one chalcogenide precursor to produce a negatively-charged chalcogen-rich nanocrystal surface, (b) removing excess anions of the chalcogenide precursor, (c) introducing a metal salt to bind a divalent metal cation to the negatively-charged chalcogen-rich nanocrystal surface to regenerate a positively-charged metal-rich nanocrystal surface, and (d) removing excess divalent metal cations of the metal acetate salt.

In one embodiment, the method further includes (e) treating the positively-charged metal-rich nanocrystal surface with oleic acid to bind oleic acid ligands thereon. In one embodiment, steps (a) to (e) are repeated a plurality of times to form nanocrystals with metal-rich surfaces and oleic acid ligands of predetermined thickness for providing solubility in non-polar organic solvents. In one embodiment, steps (a) to (d) are repeated a plurality of times to form nanocrystals with metal-rich surfaces of predetermined thickness. In one embodiment, the metal salt is a metal acetate salt. In one embodiment, the polar protic solvent comprises at least one of ammonia, N-methylformamide (NMF), t-butanol, n-propanol, ethanol, methanol, acetic acid, or water. In one embodiment, the chalcogenide precursor includes at least one of sulfur, selenium, or tellurium.

In one embodiment, the chalcogenide precursor comprises at least one material selected from the group consisting of $(NH_4)_2S$; $M_2E$ or MEH, where M is Li, Na, K, Rb, Cs, or hydrazinium and E is O, OH, S, SH, Se, SeH, Te, or TeH; salts of $(M_xE_y)_n$-, where M is a metal including Cd, Sn, In, Cu, Zn Ga, Hg, or Sb, E is O, OH, S, SH, Se, SeH, Te, or TeH, n is an anionic charge number, and x and y are the number of stoichiometric units; and metal pnictide units including Li, Na, K, Rb, Cs, or hydrazinium salts of $[M_xP_y]_n$—, where M is a metal including Zn, Cd, Hg, In, Sn, Ga, or Bi, P is a pnictide, P, As, or Sb, n is an anionic charge number, and x and y are the number of stoichiometric units. In one embodiment, the metal salt includes at least one of cadmium, zinc, tin, or lead. In one embodiment, the steps of (a) to (d) are performed at a temperature in the range of 20° C. to 50° C.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

The present disclosure describes a new method for forming superlattice and aperiodic inorganic structures through precise and sequential conformal coating of colloidal quantum wells (i.e. nanoplatelets). Using the methods described herein, superlattice and aperiodic inorganic structures may be formed such that the number of atomic layers are precisely defined in thickness—the surface of the nanoplatelets have no step edges and are atomically flat. Unlike layer-by-layer techniques or nanocrystal self-assembly, each inorganic layer is chemically bonded to its neighbors. The superlattice and aperiodic inorganic structures of the present disclosures are also distinct from Au—Cu and Pd—Cu metal superlattices or $Ag_2S$/CdS nanocrystal superlattices because layer formation may be controlled chemically at each step via Frank-van der Merwe growth (single layer epitaxy), rather than through self-segregation. Moreover, use of colloidal quantum wells rather than substrates traditionally used in physical vapor deposition (PVD) methods, provides an atomically flat, effectively planar epitaxial surface for the growth of planar superlattices. The size of the colloidal quantum well used for forming colloidal superlattices may be varied in surface area from about 25 $nm^2$ to greater than 1000 $nm^2$ with a thickness in the range of 2-11 monolayers (MLs). The materials, sizes and structural characteristics used in the present disclosure are preferentially used in the formation of colloidal superlattices because they are less likely to show edge-related perturbations of the quantum well structure.

Thus, the present disclosure describes an alternative means of achieving desired layered structures using solution chemistry and low temperatures. Unlike other solution-based methods, the formation of the layered structures described herein is achieved with atomic-layer precision. These advantages over existing vapor- and solution-based techniques allow a much lower energy intensity and cost in the fabrication of layered structures, and specifically superlattice and aperiodic inorganic structures, without sacrificing control.

Figure 1A:
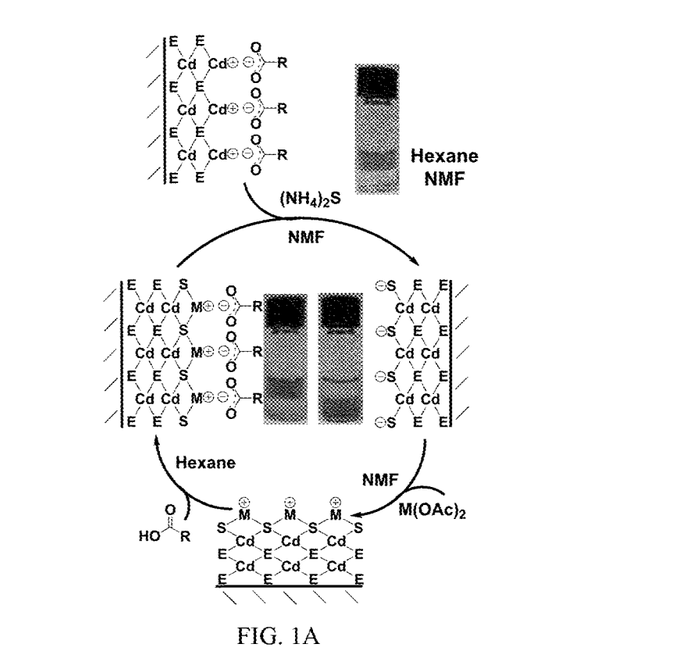
FIG. 1A illustrates a schematic of sequential layer formation of metal chalcogenide layer on top of nanocrystals, according to one embodiment of the present disclosure. One cycle constitutes a full monolayer (ML).

FIG. 1A illustrates a schematic of sequential layer formation of metal chalcogenide layer on top of nanocrystals, according to one embodiment of the present disclosure. As is shown, the atomic precision of the colloidal quantum well translates to the desired superlattice structure through the composition of each anion and cation layer using solution-phase atomic layer deposition (ALD), alternately called saturated ionic layer adsorption. In one embodiment, solution-phase colloidal ALD (c-ALD) is utilized where rapid, self-limiting reactions terminate nanocrystal surface end-groups with either anions or cations of the desired composition. In one embodiment, c-ALD is performed within a time in the range of one second to ten minutes. In one embodiment, c-ALD is performed within a time in the range of 1 second to 1 min or 1 min to 2 min or 2 min to 3 min or 3 min to 4 min or 4 min to 5 min or 5 min to 6 min or 6 min to 7 min or 7 min to 8 min or 8 min to 9 min or 9 min to 10 min. Each deposition half-cycle forms a conformal atomic layer on the substrate, followed by purge steps to remove excess reagent (i.e. excess anions or cations are purged after each reaction step). Choice of chemical precursor allows control of chemical composition of the layer and the scale or thickness of each layer is determined by the number of deposition cycles at the scale of a single layer of atoms.

c-ALD is distinct from other sequential deposition techniques, such as successive ion layer adsorption and reaction (SILAR) deposition, where precursor reagents are limiting. Because an excess of anion or cation reactant is present, a more conformal layer of the desired species may be deposited without any precise knowledge of the substrate surface area. Furthermore, c-ALD may also be generalized to many substrates including dispersed colloidal particles of planar and non-planar geometries, powders, and thin films allowing formation of layered coatings with atomic precision on surfaces of arbitrary geometry, size, and mechanical flexibility. Reactions using c-ALD are coupled to phase transfer between non-polar and polar solvent phases; as a result, simple verification of surface termination is provided and purging excess unreacted precursors is facilitated. Single-phase processing is also contemplated.

In one embodiment, the starting nanocrystals are synthesized with metal-rich surfaces and oleic acid ligands to provide solubility in nonpolar organic solvents (e.g., pentanes, hexanes, benzene, toluene, diethyl ether, and the like). In one embodiment, the nanocrystals are transferred to a polar protic solvent using at least one chalcogenide precursor to produce a negatively-charged chalcogen-rich nanocrystal surface. The polar protic solvent may be at least one of ammonia, N-methylformamide (NMF), formamide, hydrazine, N,N-dimethylformamide, propylene carbonate, or water. In one embodiment, the chalcogenide precursor includes at least one of sulfur, selenium, or tellurium. In one embodiment, the chalcogenide precursor is ammonium sulfide (($NH_4$)$_2$S); however, other contemplated chalcogenide precursors include: $M_2E$ or MEH, where M may be Li, Na, K, Rb, Cs, or hydrazinium and E may be O (or OH), S (or SH), Se (SeH), or Te (TeH), metal-chalcogenide units such as Li, Na, K, Rb, Cs, hydrazinium (or its derivatives), ammonium (or its derivatives), formadinium (or its derivatives), and salts of $(M_xE_y)_n$-, where M is a metal including Cd, Sn, In, Cu, Zn Ga, Hg, or Sb, E may be O (or OH), S (or SH), Se (SeH), or Te (TeH), n represents an anionic charge number, and x and y represent the number of stoichiometric units. Also contemplated are metal pnictide units such as Li, Na, K, Rb, Cs, or hydrazinium salts of $[M_xP_y]_n$—, where M is a metal including Zn, Cd, Hg, In, Sn, Ga, or Bi, P is a pnictide, P, As, or Sb, n represents an anionic charge number, and x and y represent the number of stoichiometric units.

After purging excess anions of the chalcogenide precursor, a metal salt or a metal acetate salt is introduced to bind a divalent metal cation with the negatively-charged chalcogen-rich nanocrystal surface. As a result, a positively-charged metal-rich nanocrystal surface is regenerated. In one embodiment, the metal acetate salt includes at least one of cadmium (Cd), zinc (Zn), tin (Sn), and lead (Pb). In one embodiment, the metal salt is of the form $M_xR_y$, where M may be ammonium (or its derivatives), formadinium (or its derivatives), hydrazinium (or its derivatives), Zn, Cd, Hg, Sn, Pb, In, Al, Ga, Cu, Ag, or Au, R is an anion such as Cl, Br, I, $PF_6$, $BF_4$, acetate, triflate, or acetylacetonate, and x and y represent the number of stoichiometric units. One challenge observed in this binding step of the metal layer is obtaining high binding efficacy and sufficiently small strain and lattice match, while at the same time, avoiding cation exchange and particle dissolution. Traditionally, alloying metal chalcogenides (e.g., Cd and Zn) in nanocrystals typically occurs at elevated temperatures (e.g., greater than 200° C.) and thus, higher energy inputs, to initiate thermally-induced decomposition. The present disclosure describes a c-ALD method occurring at 20-50° C., depending on the metal cation. At these lower temperatures, reactivity of the precursor is sufficient for alloying metal chalcogenides in nanocrystals. Furthermore, etching is also avoided due to relatively poor solubility of II-VI chalcogenides in polar solvents. The present disclosure describes a c-ALD method utilizing modestly acidic and basic conditions, which allow the chalcogenides to remain relatively stable.

Excess divalent metal cations of the metal acetate salt are subsequently purged and then the positively-charged metal-rich nanocrystal surface is treated with oleic acid to bind oleic acid ligands thereon (i.e. binding as an oleate). In one embodiment, the above-described steps are repeated a plurality of times to form nanocrystals with metal-rich surfaces and oleic acid ligands of predetermined thickness for providing solubility in non-polar organic solvents. In one embodiment, each deposition cycle includes utilizing a chalcogenide precursor, utilizing a metal salt or a metal acetate salt, and utilizing oleic acid. In one embodiment, each deposition cycle only includes utilizing a chalcogenide precursor and utilizing a metal salt or a metal acetate salt.

Figure 1B:
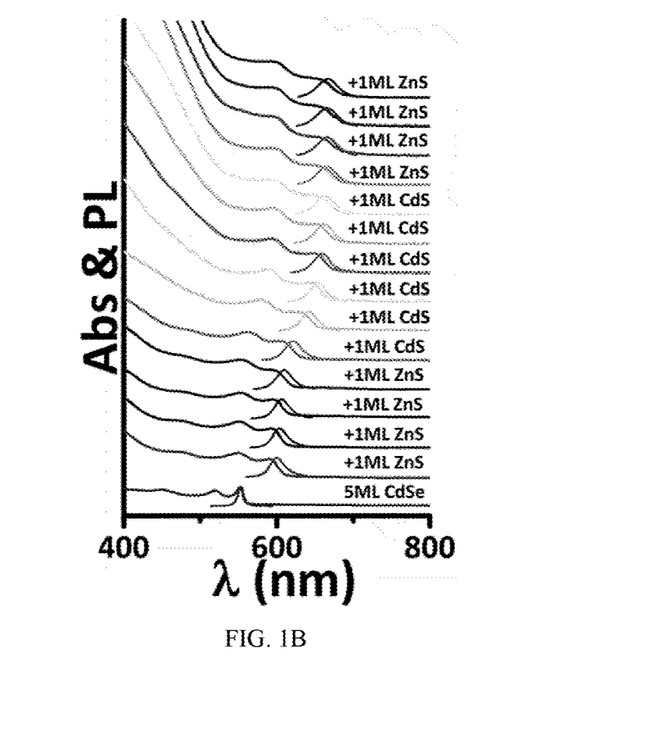
FIG. 1B illustrates absorption and photoluminescence (PL) spectra of layered structures starting with 5 ML thick CdSe nanoplatelets (NPLs) and sequential addition of 14 MLs of ZnS and CdS, according to one embodiment of the present disclosure.

Verification of the above-described c-ALD procedure may be determined using optical microscopy techniques of the sample as each successive layer is added. For example, FIG. 1B illustrates absorption and photoluminescence (PL) spectra of layered structures starting with 5 ML thick CdSe nanoplatelets (NPLs) and sequential addition of 14 MLs of ZnS and CdS. Starting with a 5 monolayer (ML) thick CdSe nanoplatelets (NPLs) sample, the sample was coated, in succession, with 4 ML ZnS, 6 ML CdS, and 4 ML ZnS. For such a wide-gap material, after the first monolayer red-shifts the absorption and emission, additional ZnS layers have little electronic effect, because the exciton is strongly confined to the CdSe layer. However, the CdS layers induce a more continuous red-shift, as the conduction band of CdS and CdSe are close in energy and electron delocalization may occur. CdS layers also dramatically increase the absorption in the blue spectral window. Photoluminescence excitation spectra collected at the emission maximum and the red edge of the emission curve demonstrate that the ensemble retains an atomically-precise quantum well electronic structure of the starting material. Red-shift and blue-shift refer to changes in observed spectral properties, i.e. shifting to longer wavelength (red) and lower energy or shorter wavelength (blue) and higher energy.

Figure 2A:
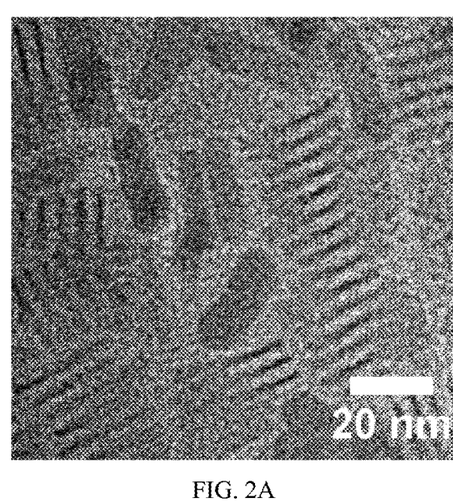
FIGS. 2A-2D illustrate transmission electron microscope (TEM) micrographs of 5 ML thick CdSe NPLs (FIG. 2A), 4 ML thick CdS NPLs (FIG. 2B), 5 ML thick CdSe/4 ML thick ZnS/6 ML thick CdS/4 ML thick ZnS structures (FIG. 2C), and 4 ML thick CdS/4 ML thick ZnS/4 ML thick CdS structures (FIG. 2D).
Figure 2B:
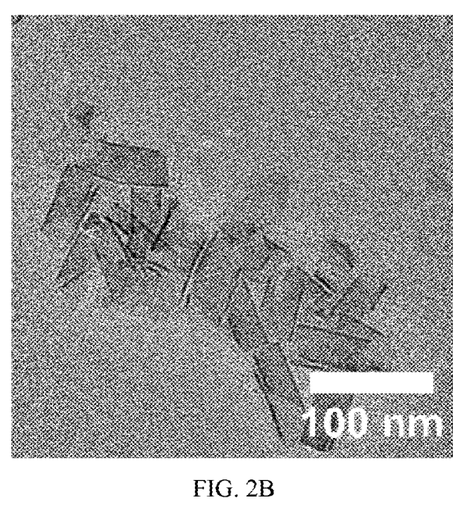

FIGS. 2A-2D illustrate transmission electron microscope (TEM) micrographs of structures produced according to the c-ALD methods described herein. Starting structures prior to processing with c-ALD are shown in FIG. 2A (5 ML thick CdSe NPLs) and FIG. 2B (4 ML thick CdS NPLs). Due to large anisotropic van der Waals attractions between the NPLs, 5 ML thick CdSe NPLs (FIG. 2A) display substantial interfacial stacking and 4 ML thick CdS NPLs (FIG. 2B) show edges rolled into scrolls. The final products of 5 ML thick CdSe/4 ML thick ZnS/6 ML thick CdS/4 ML thick ZnS (FIG. 2C; after c-ALD to the starting structure of FIG. 2A) and 4 ML thick CdS/4 ML thick ZnS/4 ML thick CdS (FIG. 2D; after c-ALD to the starting structure of FIG. 2B) show the preserved plate structure.

Figure 2C:
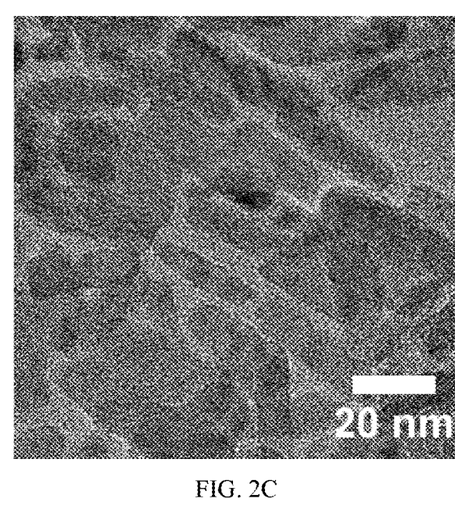
Figure 2D:
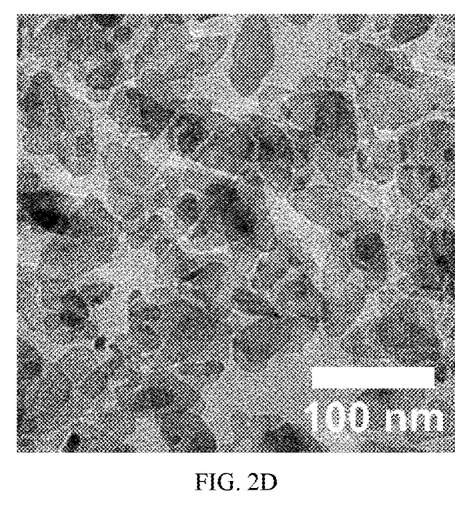
Figure 3A:
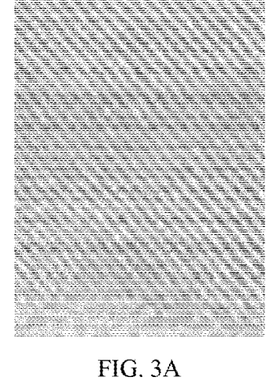
FIGS. 3A and 3B illustrate bright-field scanning transmission electron microscopy (STEM) images of 5 ML thick CdSe/4 ML thick ZnS/6 ML thick CdS/4 ML thick ZnS structures (FIG. 3A) and 4 ML thick CdS/4 ML thick ZnS/4 ML thick CdS structures (FIG. 3B).
Figure 3B:
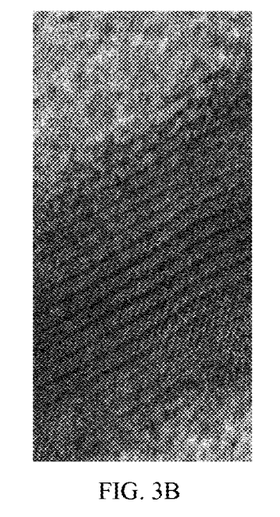
Figure 7A:
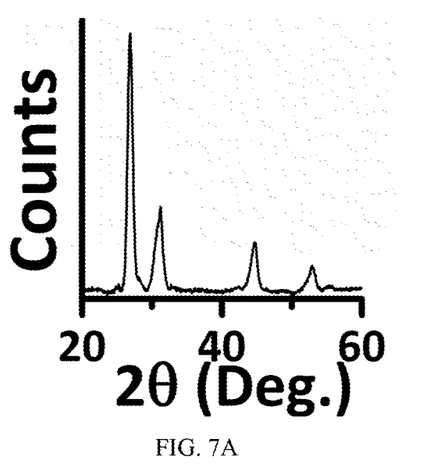
FIG. 7A illustrates x-ray diffraction data collected on a superlattice of 4 ML CdS/4 ML ZnS/4 ML CdS (corresponding to FIGS. 3A and 5B).
Figure 7B:
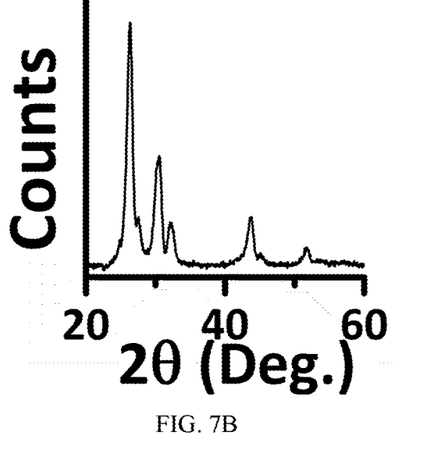
FIG. 7B illustrates x-ray diffraction data collected on a superlattice of 5 ML CdSe/4 ML ZnS/6 ML CdS/4 ML ZnS (corresponding to FIGS. 3B and 5A).

Although synthesized at low temperatures in the range of about 20° C. to about 50° C., the materials of FIGS. 2C and 2D are highly crystalline, as evidenced in the moiré fringes from two overlapping superlattices, X-ray diffraction data, and high-resolution bright-field scanning transmission electron microscopy (STEM) images of FIGS. 3A and 3B, respectively. X-ray diffraction data of FIGS. 7A and 7B shows that the samples are crystalline and conform to a zinc blend crystal structure, which is the same structure as the starting NPLs of FIGS. 2A and 2B. Particularly noteworthy is the TEM images showing that the epitaxial layers formed between CdSe and ZnS or CdS and ZnS do not generate defects, most likely because the layers are sufficiently thin to accommodate epitaxial strain without dewetting.

Figure 4A:
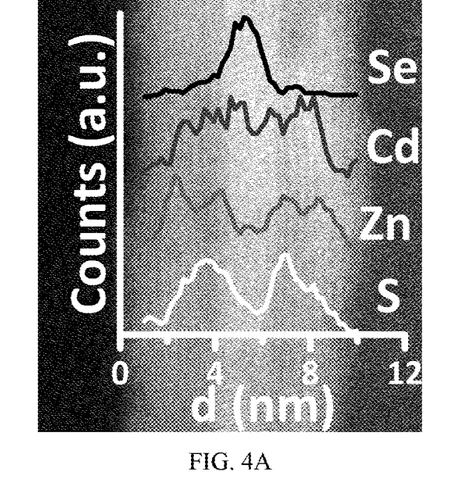
FIGS. 4A and 4B illustrate annular dark field STEM images of 5 ML thick CdSe/4 ML thick ZnS/6 ML thick CdS/4 ML thick ZnS structures (FIG. 4A) and 4 ML thick CdS/4 ML thick ZnS/4 ML thick CdS structures (FIG. 4B) with elemental data from energy-dispersive X-ray (EDX) line-scans overlayed on representative images.
Figure 4B:
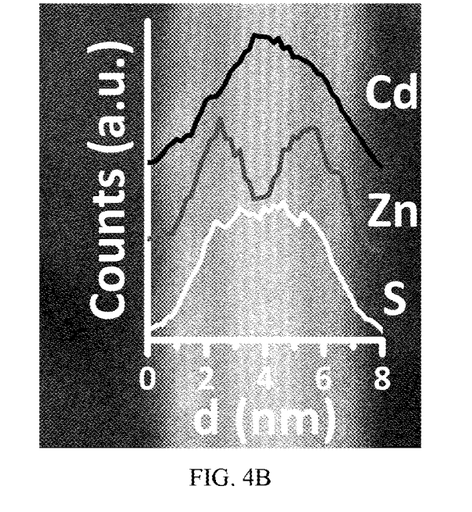

The efficacy of the reactions forming complete monolayers may be verified using annular dark field (ADF) scanning transmission electron microscopy (STEM) and elemental analysis (FIGS. 4A and 4B). The ADF-STEM images resolve clear contrast differences between the superlattice layers. Moreover, the contrast apparent in FIGS. 4A and 4B arises from the atomic mass of the atoms which deflect the electron beam. The darkest areas of FIGS. 4A and 4B have no inorganic material present. Lighter areas of the structure are composed of ZnS and darker areas are composed of CdS. Because Cd is larger than Zn, atomic columns of Cd deflect more electrons into the dark field, increasing the signal intensity in the image. FIGS. 4A and 4B confirm, by showing the individual atomic layers of the metallic ions (S having lower signal than either Cd or Zn), that the sequence of processing steps inserts a single layer of cations or anions with each half cycle. In addition to imaging techniques, energy-dispersive X-ray (EDX) line-scans were performed on the edge-oriented superlattices to confirm the composition of the different layers.

Figure 5A:
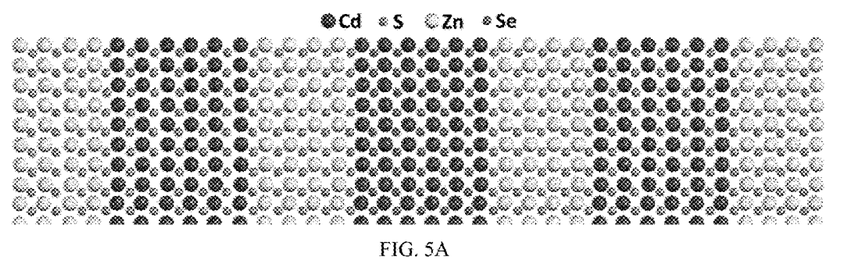
FIGS. 5A and 5B illustrate structural representations of 5 ML thick CdSe/4 ML thick ZnS/6 ML thick CdS/4 ML thick ZnS structures (FIG. 5A) and 4 ML thick CdS/4 ML thick ZnS/4 ML thick CdS structures (FIG. 5B). Atoms are not to scale.
Figure 5B:
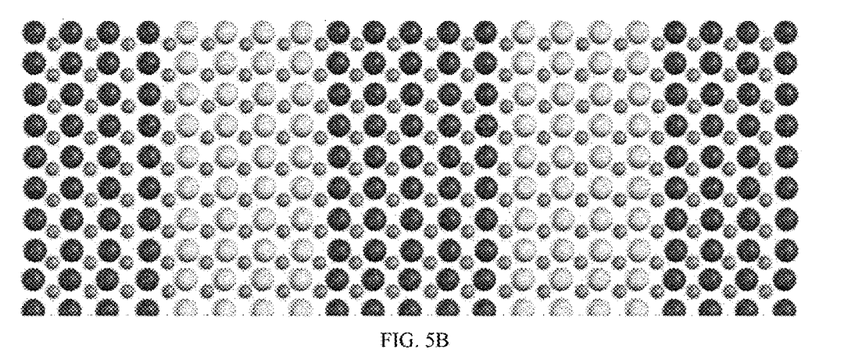

FIGS. 4A and 4B show EDX line-scan data overlaid on the ADF-STEM images of the structures of FIGS. 2C and 2D, respectively. In FIG. 4A, the brighter middle section is composed of CdSe, with the alternating layers of ZnS and CdS having a smaller contrast difference. The EDX line-scan verifies a Se rich core and S-rich shell layers; the Zn data in particular offers a clear correlation, with the ADF-image showing alternating composition of the superlattice. FIG. 4B shows similar data, where Zn content closely tracks those regions of reduced contrast (ZnS layers) apparent in the ADF-STEM image. FIGS. 5A and 5B depict structural representations of 5 ML thick CdSe/4 ML thick ZnS/6 ML thick CdS/4 ML thick ZnS structures (FIG. 5A) and 4 ML thick CdS/4 ML thick ZnS/4 ML thick CdS structures (FIG. 5B) after processing the structures of FIGS. 2A and 2B, respectively with c-ALD. Atoms are not to scale.

The colloidal superlattices fabrication techniques presented in this disclosure offer precise control over optoelectronic properties, for example in quantum wells, but without the constraints of requiring high vacuum and high temperature, as is the case with other synthesis techniques, physical vapor deposition.

Figure 6A:
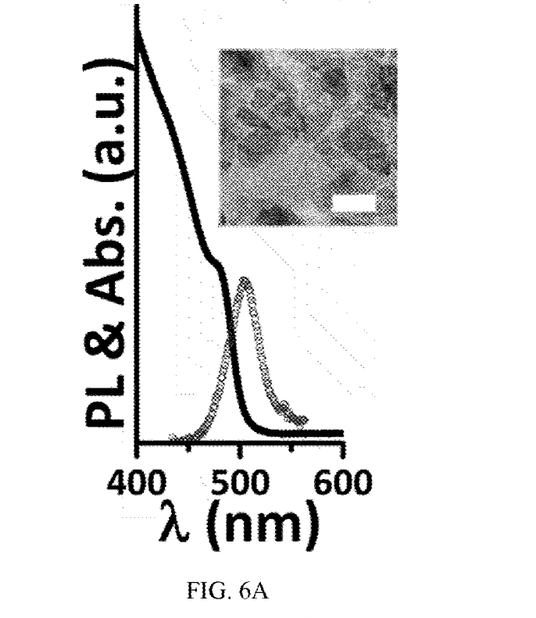
FIG. 6A illustrates absorption (solid line) and photoluminescence (PL) (open circles) of a 4 ML thick CdS/2 ML thick ZnS/4 ML thick CdS/2 ML thick ZnS colloidal superlattice. The inset of FIG. 6A shows a TEM image of the sample (scale bar is 50 nm).
Figure 6B:
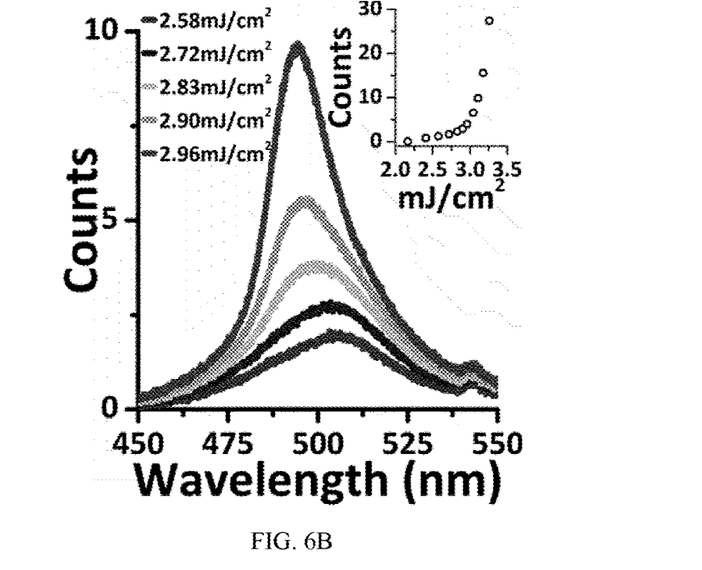
FIG. 6B illustrates emission from stripe-illuminated film of colloidal superlattices showing the onset of amplified spontaneous emission. The inset of FIG. 6B shows integrated emission counts versus input energy density.

One example is the observation of stimulated emission with negative biexciton binding energy in colloidal superlattice thin films in superlattices with a (2 ML thick ZnS/4 ML thick CdS)$_3$/2 ML thick ZnS structure. FIG. 6A illustrates absorption (solid line) and photoluminescence (PL) (open circles) of a 4 ML thick CdS/2 ML thick ZnS/4 ML thick CdS/2 ML thick ZnS colloidal superlattice under low fluence. The inset of FIG. 6A shows a TEM image of the sample (scale bar is 50 nm). FIG. 6B illustrates fluence-dependent emission from a stripe-illuminated 100 nm thick film of the same colloidal superlattices as in FIG. 6A showing the onset of amplified spontaneous emission (ASE) through the blue-shift and sharpening of the emission peak as well as a non-linear increase in intensity above the ASE threshold at 2.7 mJ/cm$^2$ (inset of FIG. 6B—integrated emission counts versus input energy density). Although colloidal nanoplatelets, including 4 ML thick CdS, show an attractive biexciton (red-shift of ASE), the data in FIGS. 6A and 6B demonstrate a repulsive biexciton, which is typically observed for type II heterostructures. Here, the subtle differences between inner and outer CdS quantum wells dictates a repulsive biexciton, which yields the blue-shift of the ASE peak.

The present disclosure describes a new method for forming superlattice and aperiodic inorganic structures through precise and sequential conformal coating of colloidal quantum wells. Specifically, atomically-precise superlattice structures are synthesized from colloidal quantum wells using c-ALD. It is understood that the present disclosure should not be limited to the application described herein, as c-ALD may be applied to other surfaces and structures such as core/crown structures, nanorings, and metal chalcogenide clusters to develop superlattice structures with more complex modulation of electronic structure and topology (e.g., radial or toroidal superlattices).

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

References herein to the positions of elements (i.e. "top," "bottom," "above," "below," "on," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed:

1. A method for forming inorganic structures, comprising:
    (a) transferring nanocrystals to a polar protic solvent using a chalcogenide precursor to produce a negatively-charged nanocrystal surface comprising negatively-charged chalcogen atoms bonded to metal atoms of the nanocrystal located on the nanocrystal surface;
    (b) removing excess anions of the chalcogenide precursor;
    (c) introducing a divalent metal salt to bind divalent metal cations to the negatively-charged chalcogen atoms bonded to the nanocrystal surface such that a metal chalcogenide monolayer is deposited on the nanocrystal surface; and
    (d) removing excess divalent metal cations of the divalent metal salt.

2. The method of claim 1, wherein the nanocrystals comprise a metal, and wherein the method further comprises: (e) treating the nanocrystal surface with oleic acid to bind oleic acid ligands to the metal of the metal chalcogenide monolayer so as to provide solubility in non-polar organic solvents.

3. The method of claim 2, wherein steps (a) to (e) are repeated a plurality of times to deposit a plurality of metal chalcogenide monolayers on the nanocrystal surface.

4. The method of claim 1, wherein the divalent metal salt is a metal acetate salt.

5. The method of claim 1, wherein the polar protic solvent comprises at least one of ammonia, N-methylformamide (NMF), t-butanol, n-propanol, ethanol, methanol, acetic acid, or water.

6. The method of claim 1, wherein the chalcogenide precursor is selected from the group consisting of sulfur, selenium, and tellurium.

7. The method of claim 1, wherein the chalcogenide precursor comprises a material selected from the group consisting of $(NH_4)_2S$; $M_2E$ or MEH, where M is Li, Na, K, Rb, Cs, or hydrazinium and E is O, OH, S, SH, Se, SeH, Te, or TeH; salts of $(M_xE_y)_n$-, where M is a metal including Cd, Sn, In, Cu, Zn Ga, Hg, or Sb, E is O, OH, S, SH, Se, SeH, Te, or TeH, n is an anionic charge number, and x and y are the number of stoichiometric units; and metal pnictide units including Li, Na, K, Rb, Cs, or hydrazinium salts of $[M_xP_y]_n{-}$, where M is a metal including Zn, Cd, Hg, In, Sn, Ga, or Bi, P is a pnictide, P, As, or Sb, n is an anionic charge number, and x and y are the number of stoichiometric units.

8. The method of claim 1, wherein the divalent metal salt includes at least one of is selected from a group consisting of cadmium, zinc, tin, and lead.

9. The method of claim 1, wherein the steps of (a) to (d) are performed at a temperature in the range of 20° C. to 50° C.

\* \* \* \* \*